(12) United States Patent
Karmaker et al.

(10) Patent No.: US 6,872,076 B2
(45) Date of Patent: Mar. 29, 2005

(54) DENTAL BRIDGES COMPRISING FIBER REINFORCED FRAMEWORKS WITH FIBER OR PARTICULATE REINFORCED VENEERS

(75) Inventors: Ajit Karmaker, Wallingford, CT (US); Arun Prasad, Cheshire, CT (US); Gregg Daskalon, Orange, CT (US)

(73) Assignee: Jeneric/Pentron Inc., Wallingford, CT (US)

( * ) Notice: Subject to any disclaimer, the term of this patent is extended or adjusted under 35 U.S.C. 154(b) by 125 days.

(21) Appl. No.: 10/002,421

(22) Filed: Oct. 25, 2001

(65) Prior Publication Data

US 2002/0082316 A1 Jun. 27, 2002

Related U.S. Application Data

(62) Division of application No. 09/270,853, filed on Mar. 17, 1999, now Pat. No. 6,362,250.
(60) Provisional application No. 60/078,347, filed on Mar. 17, 1998.

(51) Int. Cl.[7] .............................................. A61C 13/87
(52) U.S. Cl. ................................ 433/201.1; 433/202.1; 433/206; 433/228.1
(58) Field of Search .......................... 433/201.1, 202.1, 433/206, 228.1, 205

(56) References Cited

U.S. PATENT DOCUMENTS

| | | | |
|---|---|---|---|
| 3,066,112 A | 11/1962 | Bowen | 523/116 |
| 3,179,623 A | 4/1965 | Bowen | 523/205 |
| 3,194,784 A | 7/1965 | Bowen | 523/116 |
| 3,715,331 A | 2/1973 | Molnar | 523/117 |
| 3,751,399 A | 8/1973 | Lee et al. | 106/35 |
| 3,926,906 A | 12/1975 | Lee, II et al. | 523/116 |
| 4,107,845 A | 8/1978 | Lee, Jr. et al. | 523/116 |
| 4,297,266 A | 10/1981 | Ibsen et al. | 523/115 |
| 4,445,863 A | 5/1984 | Lang et al. | 433/212 |
| 4,544,359 A | 10/1985 | Waknine | 523/118 |
| 4,547,531 A | 10/1985 | Waknine | 523/116 |
| 4,585,417 A | 4/1986 | Sozio et al. | 433/202.1 |
| 4,711,913 A | 12/1987 | Tateosian et al. | 522/14 |
| 4,717,341 A | 1/1988 | Goldberg et al. | 433/4 |
| 4,894,012 A | 1/1990 | Goldberg et al. | 433/215 |
| 5,127,834 A | 7/1992 | Hasegawa et al. | 433/202.1 |
| 5,171,147 A | 12/1992 | Burgess | 433/180 |
| 5,266,609 A | 11/1993 | Hall et al. | 523/116 |
| 5,276,068 A | 1/1994 | Waknine | 522/23 |
| 5,304,586 A | 4/1994 | Hammesfahr et al. | 523/117 |
| 5,444,104 A | 8/1995 | Waknine | 522/24 |
| 6,013,694 A | 1/2000 | Jia et al. | 523/116 |
| 6,039,569 A | 3/2000 | Prasad et al. | 433/180 |
| 6,186,790 B1 * | 2/2001 | Karmaker et al. | 433/215 |
| 6,200,136 B1 * | 3/2001 | Prasad et al. | 433/180 |

FOREIGN PATENT DOCUMENTS

WO   WO 96/15731   5/1996

OTHER PUBLICATIONS

Junro Yamashita, et al. "A comparison of in vivo and in vitro strain with posterior fixed partial dentures" The Journal of Prosthetic Dentistry, Mar. 1997, vol. 77, No. 3, pp 250–255.
Edited by Floyd A. Peyton, et al, "Restorative dental materials", pp. 121–133 (1971).
Ajit Karmaker, et al, Patent disclosure "Means of improving the strength and longevity of multi–unit bridges involving fiber reinforced composite (FRC) and veneer of particulate filled composite (PFC)".

* cited by examiner

*Primary Examiner*—Peter Szekely
(74) *Attorney, Agent, or Firm*—Cantor Colburn LLP

(57) ABSTRACT

A dental restoration comprising a fiber reinforced composite framework and one or more of a randomly dispersed, fiber-filled veneer, a soft particulate filled composite veneer having a strain to failure greater than that of FRC framework and/or a brittle particulate filled composite veneer having a strain to failure value less than that of the FRC framework. The fiber filled veneer is advantageously placed beneath the framework, the soft veneer is advantageously pled where tensile stresses are expected to occur, while the brittle particulate filled veneer is placed where compressive stresses are expected to occur.

17 Claims, 3 Drawing Sheets

DENTAL BRIDGES COMPRISING FIBER REINFORCED FRAMEWORKS WITH FIBER OR PARTICULATE REINFORCED VENEERS

This divisional application claims priority to U.S. patent application Ser. No. 09/270,853 filed on Mar. 17, 1999, now U.S. Pat. No. 6,362,250 B1. which claims priority to Provisional Application Ser. No. 60/078,347 filed on Mar. 17, 1998 both of which are hereby incorporated by reference.

BACKGROUND OF THE INVENTION

1. Field of the Invention

This invention relates to composite materials for dental restorations. In particular, this invention relates to fiber reinforced prosthodontic frameworks comprising a fiber reinforced composite framework and at least one or more filled composite veneers.

2. Brief Discussion of the Art

Fiber-reinforced composites have found increasing use in the field of materials for dental restorations, and are described, for example, in U.S. Pat. Nos. 4,717,341 and 4,894,012 to Goldberg et al. both of which are hereby incorporated by reference in their entirety. Fiber-reinforced composites generally comprise at least two components, a polymeric matrix and fibers embedded within the matrix. The polymeric matrix may be selected from those known for use in composite dental materials, for example polyamides, polyesters, polyolefins, polyimides, polyarylates, polyurethanes, vinyl esters or epoxy-based materials. The fibers used to reinforce composite material may comprises glass, carbon, or polymer fibers such as polyaramide and polyethylene, as well as other natural and synthetic fibers.

Fiber reinforced composite material provides several advantages, most notably increased strength and stiffness. As described in U.S. Pat. Nos. 4,717,341 and 4,894,012 to Goldberg et al., such materials accordingly are used as structural components in a variety of dental appliances, taking the form of bars, wires, beams, posts, clasps, and laminates for use in traditional bridges, crowns, artificial teeth, dentures, veneers, and the like. They have also been used in connection with orthodontic retainers, bridges, space maintainers, splints, and the like. In these applications, the fibers preferably take the form of long, continuous filaments, although the filaments may be shorter than 5 millimeters. Where the composites take the form of elongated wires, the fibers are at least partially aligned and oriented along the longitudinal dimensions of the wire. However, depending on the end use of the composite material, the fibers may also be otherwise oriented, including being normal or perpendicular to that dimension.

Fiber reinforced composites are particularly useful as structural components in dental bridges. In the dental arts, a bridge is a device for the restoration and replacement of one or more natural teeth, replacing at least one missing tooth and supported on either side by the remaining teeth. A bridge generally comprises a pontic for replacement of the missing tooth, and a connector on either side of the pontic which connects the pontic to a retaining member such as a crown formed on an abutment tooth adjacent the pontic. By their nature, bridges must be aesthetic, as well as strong, in order to withstand forces generated by chewing and to maintain the positions of the abutting teeth.

The combination of a fiber reinforced framework and particulate filled composite veneer offers good strength and excellent aesthetics. These systems result in a decrease in the antagonistic wear of opposite teeth compared to the use of metal-porcelain bridges. These systems also provide higher impact energy, and are free of leaching of metal ions. The tensile strength and elastic modulus of uniaxially oriented continuous glass fiber reinforced BIS-GMA are competitive with those of stainless steel and some titanium alloys. Such bridges are described for example in co-assigned U.S. Provisional Patent Application No. 60/055,590, filed Aug. 12, 1997, now U.S. Pat. No. 6,039,569, and exemplified by the FIBREKOR® system for making dental bridges commercially available from Jeneric/Pentron Inc., Wallingford, Conn.

An important consideration in constructing a single or multi exerted on the bridge. Dental restorations must be able to withstand the normal mastication forces and stresses that exist within an oral environment, which have been described, for example, in "Restorative Dental Materials", 4th ed., edited by F. A. Peyton and R. G. Craig, pp. 121–133 (1971). Different stresses are observed during mastication of different types of food, which can be experimentally measured by placing, for example, a strain gauge in inlays on the tooth. Stresses differ depending not only on the type of food, but also on the individual. For example, stress values may range from 570 to 2300 lb./inch$^2$ or from 950 to 2400 lb./inch$^2$ for a single thrust. The physical properties of dental restorations must be adequate to withstand the stresses applied by the repetitive forces of mastication. If an applied force exceeds that which the dental restoration can withstand, then fracture in the dental restoration material results. Therefore, the dental restoration must be constructed so that loads on the restoration are lower than the maximum load-bearing capability of the restoration.

An important parameter in dental bridges in particular is the flexural strength of such bridges. In a multi-unit dental bridge there is at least one pontic not supported on its gingival surface. The only supports are the two connecting areas with the adjacent abutments. Hence if a load is applied normal to any pontic surface, the bridge tends to deflect, resulting compressive stress/strain on the surface on which load is applied and tensile stress/strain on the opposite surface. This is common for any simply-supported specimen exposed to flexural testing. Because of the geometric complexity of the dental bridge and the multidirectional loads generated in different locations during chewing and mastication, the magnitudes of stress/ strain vary in different locations.

Consequently, while well-suited for their intended purposes, the design of many currently manufactured dental bridges suffers from a framework material having a flexural modulus higher than that of the particulate-filled veneer material; and/or the particulate-filled veneer material having a strain to failure value lower than that of the fiber-reinforced framework material. There is a need to make the particulate filled composites compatible with the fiber reinforced composite structural frameworks in the strain to failure value to provide high strength to the dental restoration. It is desirable to increase strength of dental restorations without complicating or increasing the number of steps used in the fabrication of dental restorations. Such improvements would result in dental bridges which can better withstand the forces and strains that accompany the chewing of food and other activities, and which provide maximum performance for their intended use.

SUMMARY OF THE INVENTION

The above-described drawbacks and deficiencies of the prior art are alleviated by the fiber reinforced prosthodontics of the present invention, wherein the prosthodontic may include a fiber-reinforced composite structural component or framework and a veneer comprising a filler of particulate and/or randomly dispersed fibers. The veneer may be a "brittle" veneer of particulate filled composite having a strain to failure value less than that of the fiber reinforced framework and/or a "soft" veneer of particulate filled composite having a strain to failure value greater than that of the fiber reinforced framework. In an important feature of this embodiment, the prosthodontic is constructed depending on its intended location within the patient's mouth, and thus the expected forces that will impact the prosthodontia. In particular, a soft particulate filled composite having a higher deflection value than the fiber reinforced composite is used in the areas where higher tensile strain is expected. On the other hand, a hard particulate filled composite having a high compressive strength is used in areas subject to high compressive strain and wear.

In another embodiment, a soft particulate veneer is provided which comprises randomly dispersed fibers. The fibers may have a maximum length of about ¼ inch, preferably in a range of from about 0.01 to about 6 millimeters, and more preferably in the range of from about 20 to about 1000 microns and a diameter below about 20 microns, preferably in the range of from about 5 to about 10 microns. The veneer has strain to failure values compatible with the fiber reinforced composite structural components and/or frameworks.

A dental bridge is further provided using a unidirectional fiber reinforced composite structural component wherein the interior portion of the pontic and the abutments is fabricated of the randomly dispersed fiber filled composite resin disclosed herein.

In yet another embodiment herein, a process for manufacturing a dental restoration comprises providing a structural component for use as the framework of a dental restoration such as a bridge. Composite resin filled with a fibrous filler of randomly dispersed fibers is disposed underneath and on the structural component in the form of pontics and abutments and cured thereon to form a framework for a dental bridge. The bridge is given the final anatomical contour by veneering with a particulate filled composite.

In still another embodiment herein, a crown having an interior segment of this randomly-dispersed fibrous filled composite is fabricated.

BRIEF DESCRIPTION OF THE DRAWINGS

For the purpose of illustrating the invention, there are shown in the drawing forms which are presently preferred; it being understood, however, that this invention is not limited to the precise arrangements and instrumentalities shown. Referring now to the drawings wherein like elements are numbered alike in the several FIGURES.

DETAILED DESCRIPTION OF THE INVENTION

Figure 1:
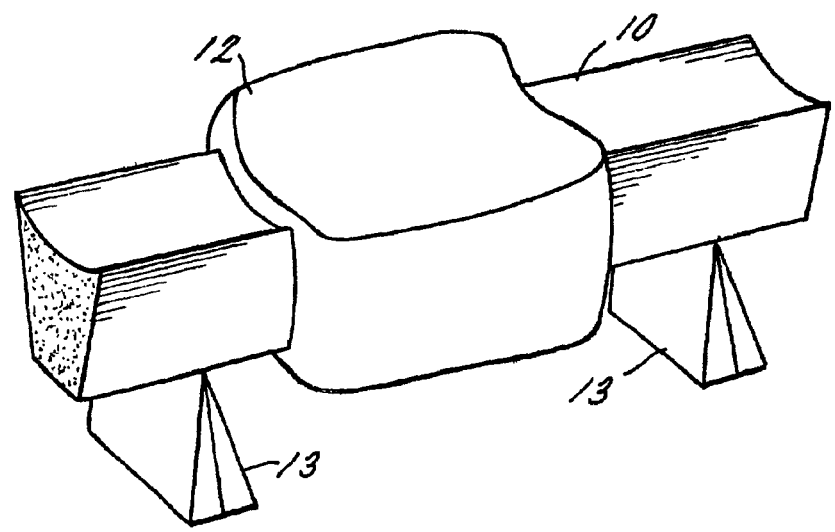
FIG. 1 is a perspective view of a unidirectional fiber-reinforced structural component (framework) and a fiber-filled composite veneer in the shape of a pontic in accordance with the present invention.

The prosthodontic dental restoration in accordance with the present invention comprises a fiber reinforced composite (hereinafter "FRC") structural component or framework and may include at least one veneer. As used herein, "veneer" is used to refer to that part of the restoration comprising a randomly dispersed, short fiber-filled and/or particulate-filled composite, as distinguished from the FRC. In one embodiment, the veneer comprises a randomly dispersed, short fiber-filled and/or particulate-filled composite (hereinafter "PFC") having a strain to failure value greater than that of the fiber reinforced framework, referred to herein as a "soft" PFC. The dental restoration may further comprise a veneer of a particulate-filled composite having a strain to failure value less than that of the FRC framework, referred to herein as a "brittle" PFC. As will be described in more detail below, the placement of the soft and brittle PFCs onto the framework depends on the intended location of the prosthodontia in the patient's mouth, which affects the type and degree of stress/strain placed on the prosthodontia.

In another embodiment, the veneer comprises a polymeric matrix component and a fibrous filler component wherein the fibers are less than about ¼ inch in length and are randomly-dispersed in the resin. Preferably, the veneer is fabricated around the structural component as in a pontic and/or as abutments.

1. Fiber Reinforced Composite (FRC) Structural Component

The FRC structural component of the present invention comprises a polymeric matrix and fibers embedded within the matrix. The polymeric matrix is selected from those known in the art of dental materials, including but not being limited to polyamides, polyesters, polyolefins, polyimides, polyarylates, polyurethanes, vinyl esters or epoxy-based materials. Other polymeric matrices include styrene, styrene acrylonitrile, acrylonitrile butadiene styrene polymers ("ABS polymers"), polysulfones, polyacetals, polycarbonates, polyphenylene sulfides, and the like.

Preferred matrix materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine, all of which are herein incorporated by reference in their entirety. An especially preferred methacrylate monomer is the condensation product of bisphenol A and glycidyl methacrylate, 2,2'-bis [4-(3-methacryloxy-2-hydroxypropoxy) phenyl]propane (hereinafter abbreviated "BIS-GMA"). Polyurethane dimethacrylates (hereinafter abbreviated "PUDMA") are also commonly-used principal polymers suitable for use in the present invention.

Use of an ethoxylated bisphenol A dimethacrylate allows the relative amounts of dimethacrylate oligomer to be decreased in comparison to other resin formulations, for example those disclosed in U.S. Pat. Nos. 5,276,068 and 5,444,104 to Waknine. Use of the ethoxylated monomer also unexpectedly improves the wettability of the cured resin composition, thereby resulting in better filler incorporation. The cured resins thus obtained have improved water sorption characteristics, improved stain resistance, and further possess excellent wearability.

The ethoxylated bisphenol A dimethacrylate in accordance with the present invention has the structure

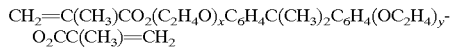

wherein x+y is an integer from 2 to 20, and preferably from 2 to 7. Such material is available from Sartomer®, under the trade name SR348 or SR480, or from Esschem.

The preferred dimethacrylate oligomer for use with the ethoxylated bisphenol A dimethacrylate of the present invention is a polycarbonate dimethacrylate condensation product obtained by the condensation reaction of a hydroxy alkyl methacrylate of the general formula $H_2CC(CH_3)C(O)O$-A-OH, in which A is a $C_1$–$C_6$ alkylene, with 1 part of a bis(chloroformate) of the formula $ClC(O)$—$(OR)_n$—$OC(O)$ Cl, in which R is a $C_2$–$C_5$ alkylene having at least two carbon atoms in its principal chain, and n is an integer from 1 to 4. By "principal chain" is meant the chain of carbon atoms serving as a bridge between the oxygen atoms. Such preferred polycarbonate dimethacrylate condensation products have been described in commonly assigned U.S. Pat. Nos. 5,276,068, and 5,444,104, the disclosures of both of which are herein incorporated by reference. A particularly preferred polycarbonate dimethacrylate is the condensation product of 2-hydroxyethylmethacrylate (2-HEMA) and triethylene glycol bis(chloroformate).

In addition to the two aforementioned monomeric components, the resinous dental compositions of the present invention can further include a diluent monomer to increase the surface wettability of the composition by decreasing the viscosity of the polymerization medium. Suitable diluents include those known in the art such as hydroxy alkyl methacrylates, for example 2-hydroxyethyl methacrylate and 2-hydroxypropyl methacrylate; ethylene glycol methacrylates, including ethylene glycol methacrylate, diethylene glycol methacrylate, tri(ethylene glycol) dimethacrylate, fluoro-triethylene glycol dimethacrylate, and tetra(ethylene glycol) dimethacrylate; diisocyanates, such as 1,6-hexamethylene diisocyanate and ethoxylated monomers such as 1,6-hexanedioldimethacrylate. Tri(ethylene glycol) dimethacrylate (TEGDMA) is particularly preferred.

The polymer matrix typically includes polymerization initiators, polymerization accelerators, ultra-violet light absorbers, anti-oxidants, and other additives well known in the art. The polymer matrices may be visible light curable, self-curing, dual curing, and vacuum, heat, and pressure curable compositions as well as any combination thereof. The visible light curable compositions include the usual polymerization initiators, polymerization accelerators, ultra-violet absorbers, fluorescent whitening agents, and the like. For example, visible light curable compositions employ light-sensitive compounds such as benzil diketones, and in particular, DL-camphorquinone in amounts ranging from about 0.05 to 0.5 weight percent. Self-curing compositions will generally contain free radical polymerization initiators such as, for example, a peroxide in amounts ranging from about 0.5 to 6 weight percent. Particularly suitable free radical initiators are lauryl peroxide, tributyl hydroperoxide and, more particularly benzoyl peroxide.

The polymerization accelerators suitable for use in the compositions of this invention are the various organic tertiary amines well known in the art. In visible light curable compositions, the tertiary amines are generally acrylate derivatives such as dimethylaminoethyl methacrylate and, particularly, diethylaminoethyl methacrylate in amounts ranging from about 0.05 to 0.5 weight percent. In the self-curing compositions, the tertiary amines are generally aromatic tertiary amines, such as dimethyl-p-toluidine, dihydroxyethyl-p-toluidine and the like, in amounts ranging from about 0.05 to about 4.0 weight percent.

It is furthermore preferred to employ an ultraviolet absorber in these resinous adhesives in amounts ranging from about 0.05 to about 5.0 weight percent. Such UV absorbers are particularly desirable in the visible light curable compositions in order to avoid discoloration of the resin from any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y. In the self-curing compositions, the polymerization accelerator can be included in the resinous composition which is used for pretreating the exposed dentin. The heat and pressure curable compositions, which are generally filled compositions, include, in addition to the monomeric components, a heat cure initiator such as benzoyl peroxide, 1,1'-azobis (cyclohexanecarbonitrile), or other free radical initiators.

The reinforcing fiber element of the fiber-reinforced composite preferably comprises glass, carbon, graphite, polyaramid, or other fibers known in the art. The FRC fibers are greater than about 100 microns, preferably greater than about 5 mm, and more preferably greater than about 10 mm, and, in contrast to the randomly dispersed fiber-filled composite veneer described below, they are not randomly dispersed. Thus, in one embodiment of the present invention, the fibers take the form of long, continuous filaments which are at least partially aligned relative to each other. Where the composites take the form of elongated bars, the fibers are at least partially (and preferably fully) aligned and oriented along the longitudinal dimensions of the bar. However, depending on the end use of the composite material, the fibers may also be otherwise oriented, for example woven, at various angles between 0 and 90° to the longitudinal fibers.

The amount of reinforcing fibers used within the composite will depend on the particular application, but preferably comprises at least about 20% by weight of the composite material. A preferred FRC for use in the present invention is glass fiber reinforced resin, commercially available under the trade name FIBREKOR® from Jeneric/Pentron, Inc., Wallingford, Conn. Other suitable fibers for FRCs in accordance with the present invention include high modulus, organic polymeric fibers, for example polyethylene fibers (available from Allied under the trade name SPECTRA) or aramid fibers (available from DuPont under the trade name KEVLAR). Preferably, the reinforcing fibers are used in accordance with U.S. Pat. Nos. 4,717,341 and 4,894,012 to Goldberg et al., the relevant portions of which are herein incorporated by reference. The polymeric matrix may further contain the particulate fillers described below in amounts of up to about 5% by weight of the total composite.

2. Veneers

The veneers of the invention comprise a polymeric matrix and may include one or more fillers embedded in the matrix. Preferably the veneers are filled with particulate filler and are referred to as Particulate Filled Composite (PFC) Veneers.

In one embodiment, the prosthodontics of the present invention comprise one or more veneers, a soft PFC veneer having a strain to failure value greater than that of a fiber reinforced framework, and a brittle PFC having a wear resistance similar to natural enamel. Each PFC comprises a polymeric matrix and a particulate filler.

Polymeric matrices suitable for use in the veneers are similar to and include those described above in connection with the FRC framework. Preferably, the FRC and PFC matrices (first and second matrix respectively) are identical or compatible, e.g., all being methacrylate based.

Suitable particulate fillers are those capable of being covalently bonded to the polymeric matrix itself or to a coupling agent that is covalently bonded to both and can include all of the inorganic fillers currently used in dental restorative materials. Examples of suitable particulate filling materials include but are not limited to those known in the art such as silica, silicate glass, quartz, barium silicate, barium sulfate, barium molybdate, barium methacrylate, strontium silicate, barium borosilicate, strontium borosilicate, borosilicate, lithium silicate, amorphous silica, ammoniated or deammoniated calcium phosphate and alumina, zirconia, tin oxide, and titania. Particularly suitable particulate fillers for dental filling-type materials prepared in accordance with this invention are those having a particle size ranging from about 0.1 to about 5.0 microns may be prepared by a series of milling steps comprising wet milling in an aqueous medium, surface etch milling and silanizing milling in a silane solution. Some of the aforementioned inorganic filling materials are disclosed in commonly-assigned U.S. Pat. Nos. 4,544,359 and 4,547,531 to Waknine, the pertinent portions of which are incorporated herein by reference. Details of the preparation of the preferred inorganic particulate filler, which comprises a mixture of from about 5 to about 20% by weight of borosilicate glass and from about 80 to about 95% by weight barium borosilicate, and has an average particle size diameter of from about 0.5 to about 5 microns, can be found in the aforementioned U.S. Pat. Nos. 4,544,539 and 4,547,531. A microfine silica or silicate of about 0.001 to 0.1 may be included to adjust handling and molding characteristics.

Suitable organic filler materials are known in the art, including for example the poly(methacrylate) fillers described in U.S. Pat. No. 3,715,331 to Molnar. A mixture of organic and inorganic filler materials may also be used. One consideration in the selection of a filler is the difference in the index of refraction of the filler material and that of the resinous matrix. In general, a more aesthetically pleasing restoration can be obtained when the difference between the index of refraction of the filler material and that of the resin matrix is small.

As discussed above, the brittle PFC has a high compressive strength and wear resistance. The brittle composite is thus preferably place in locations demanding high wear resistance. In general, the brittle PFC is more highly filled and polishable, i.e., comprises from about 70 to about 80% by weight filler of the total PFC composition, and has deflection values in the range from about 0.3 mm to about 0.5 mm as tested according to American National Standard/ American Dental Association Specification No. 27 ("ANSI/ ADA Spec. NO. 27") (on samples of 2 mm in thickness by 2 mm in width by 25 mm in length). A suitable commercially available material for use as a brittle PFC is available under the trade name SCULPTURE® from Jeneric/Pentron, Inc., Wallingford, Conn. This PFC has deflection values of about 0.2 to about 0.5 mm and further as shown in Table 3.

The soft PFC has a strain to failure value about equal to or higher than the FRC component. The strain to failure values of the soft PFC are thus dependent on the composition and volume fraction of the resin, size distribution and amount of fibrous and particulate fillers. In general, the soft PFC is less filled, comprising from about 0 to about 80% by volume filler, and preferably from about 10 to about 30% by volume filler of the total composite. A suitable soft PFC having proper strain to failure values can utilize the full support of the FRC composite as demonstrated in Example 4 below. Generally, the deflection values of the soft PFC are greater than about 0.5 mm, and preferably range from about 0.6 to about 5.0 mm, and more preferably range from about 0.6 to about 1.5 mm for a bar having dimensions of 2×2×25 mm as measured by ANSI/ADA Spec. No. 27.

In a preferred embodiment, the soft veneer comprises a polymeric matrix which is filled or partially filled with a randomly dispersed, fibrous component in addition to the particulate component. The fibrous component may comprise fibers of uniform or random length. The fibrous component preferably comprises short fibers of lengths no greater than ¼ inch. Preferably, the length of the fibers is between about 0.01 and about 6 mm. The fibers are preferably randomly dispersed throughout the resin. The fibers may be fabricated of glass, carbon, ceramic, polyaramid, or other fibers known in the art, such as polyesters, polyamides, and other natural and synthetic materials compatible with the polymeric matrix.

Some of the aforementioned fibrous materials are disclosed in commonly assigned U.S. patent application Ser. Nos. 08/907,177 (now abandoned), 09/059,492 (now abandoned), 60/055,590 (now issued as U.S. Pat. No. 6,039, 569), 08/951,414 (now issued as U.S. Pat. No. 6,013,694), and U.S. Pat. Nos. 4,717,341 and 4,894,012 all of which are incorporated by reference herein.

The fibers may further be treated, for example, thermally, chemically or mechanically etched and/or silanized, or otherwise treated such as by grafting functional monomers to obtain proper coupling between the fibers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane is A-174 (p-methacrylate propyl tri-methoxy silane), produced by OSI Specialties, NY.

The polymeric matrix is similar to those described above in connection with the FRC framework. Preferably, the matrices are identical or compatible, e.g., all being methacrylate-based. In a preferred embodiment, the polymeric matrix comprises ethoxylated bisphenol A dimethacrylate in an amount in the range from 55 to about 90 percent by weight of the total resin matrix composition, preferably in an amount in the range from about 70 to about 80 percent by weight of the total resin composition. Typically, a dimethacrylate oligomer, preferably the above-described polycarbonate dimethacrylates, is incorporated into the matrix composition in an amount from about 10 to about 45 weight percent of the total resin composition. The optional diluent monomer is typically present in an amount from about 0 to about 40 weight percent of the total resin composition.

When no diluent component is employed the preferred range for the ethoxylated bisphenol A dimethacrylates is from 65 to about 90 weight percent, and most preferably about 70 weight percent of the total resin composition, and the preferred range for the dimethacrylate oligomer is from about 10 to about 30 weight percent, and most preferably about 30 weight percent of the total resin composition.

Typical visible light curable resinous dental compositions according to this invention comprise:

(a) 10–45 weight percent of the polycarbonate dimethacrylate condensation product of triethylene glycol bis(chloroformate) and 2-hydroxyethylmethacrylate;

(b) 55–90 weight percent of ethoxylated bisphenol A dimethacrylate;
(c) 0.05–0.50 weight percent of DL-camphorquinone;
(d) 0.05–0.5 weight percent of diethylamino ethyl methacrylate; and
(e) 0.05–5 weight percent of TINUVIN P ultraviolet absorber in specific amounts within these ranges to yield about 100% by weight of a polymerization system. A particularly preferred embodiment comprises 68% by weight ethoxylated bisphenol A dimethacrylate, 30% by weight of the polycarbonate dimethacrylate condensation product of triethylene glycol bis(chloroformate) and 2-hydroxyethylmethacrylate, 0.07% by weight 2-(2-hydroxy-5-tert-octylphenyl) bezotriazole, 0.019% by weight 2,5-bis(5-tert-butyl-2-benzoxazoyl)thiophene, 0.193% by weight camphorquinone, 0.097% by weight benzil, 0.967% by weight 2,4,6-trimethyl benzoyldiphenylphosphine oxide, 0.048% by weight butylhydroxytoluene, 0.242% by weight diethylaminoethyl methacrylate, and 0.967% by weight 1,1'-azobis(cyanocyclohexane).

Preferred visible light curable compositions comprise the following components (weight percent) in specific amounts within these ranges to yield about 100% by weight of a polymerization system:

TABLE 1

| Broad Range | Preferred Range | Most Preferred | Component |
| --- | --- | --- | --- |
| 10–45 | 10–25 | 20 | Polycarbonate dimethacrylate condensation product of triethylene glycol bis(chloroformate) and 2-HEMA |
| 55–90 | 55–65 | 60 | Ethoxylated bisphenol A dimethacrylate |
| 0–40 | 10–30 | 20 | TEGDMA |
| 0.05–0.40 | 0.200–0.300 | 0.25 | Diethylaminoethyl-methacrylate |
| 0.25–4.0 | 0.500–1.500 | 1.0 | TINUVIN P (ultra-violet absorber) |
| 0.05–0.50 | 0.10–0.30 | 0.25 | 2,3-d-bornanedione or DL-camphorquinone |
| .001–.2500 | 0.00–0.20 | 0.05 | BHT |
| 0.00–0.500 | 0.00–0.2500 | 0.0097 | Fluorescent/whitening agent (UNITEX OB) |

The filled and partially filled compositions can be prepared in visible light curable formulations, self-curing, and dual curing formulations. In addition, the filled compositions can be prepared in heat pressure curing formulations. It has surprisingly been found that heat-pressure curing the filled or partially filled dental compositions of the present invention results in a material which exhibits superior physical and mechanical properties when compared to other modes of cure. The filled composite restorative materials can be prepared by admixing from about 20 to 60% by weight, preferably 25 to 40% by weight, of the unfilled visible light curable, self-curing, dual-curing or heat-pressure curable dental resin composition with from about 50 to about 80% by weight, preferably about 60 to 75% by weight of inorganic filler (fibrous plus particulate) material.

In a particularly preferred embodiment, the composite dental restorative material comprises a fibrous filler randomly dispersed in the polymeric matrix having an average length of about 0.1 to about 3 mm and a particulate filler having an average particle size of from about 0.5 to 5 microns homogeneously dispersed in the polymeric matrix, with the polymeric matrix being an organic polymerizable monomeric matrix comprising the ethoxylated dimethacrylate. In addition, a relatively small amount of fumed silica (e.g., below about 15 wt. %) is also incorporated within the monomeric matrix to improve handling characteristics. The inorganic filler primarily comprises an X-ray opaque alkali metal or alkaline earth metal silicate such as lithium alumina silicate, barium silicate, strontium silicate, barium borosilicate, strontium borosilicate, borosilicate, as well as any of the aforementioned materials. For purposes of illustration, and as the preferred silicate species, barium borosilicate will hereinafter be employed as being typical of the alkali metal or alkaline earth metal silicates which can be suitably employed in the present invention. The barium borosilicate exhibits an index of refraction close to that of the organic monomeric matrix in which it is dispersed. The filler can additionally contain a relatively small amount of borosilicate glass which imparts greater compressive strength to the resulting composite and enhances the translucency thereof thereby enabling better blending of the restorative material with the adjacent teeth. In addition, the presence of the borosilicate glass helps narrow the gap in the mismatch of refractive indices between the barium borosilicate inorganic fiber phase and the organic monomeric matrix.

The relative quantities by weight of polymeric matrix, fibrous filler, and particulate filler are set forth in Table 2 below:

TABLE 2

| Component | Range | Preferred Range | Most Preferred |
| --- | --- | --- | --- |
| Polymeric matrix | 20–60 | 30–55 | 30–50 |
| Fibrous Filler | 5–50 | 5–40 | 10–40 |
| Particulate Filler | 20–60 | 20–55 | 25–45 |

The deflection values for the soft PFC comprising particulate and random fibers is generally greater than about 0.5 mm and preferably is in the range of from about 0.6 to about 3 mm and preferably in the range of from about 0.6 to about 1.5 mm for a bar having dimension of 2×2×25 as measured by ANSI/ADA Spec. No. 27. The fibrous filled resin may be used in a variety of ways to manufacture dental materials and restorations including, but not limited to veneers, cements, crowns, inlays and onlays. Preferably, the fibrous filled resin is used in combination with a structural element or framework comprised of a fiber reinforced composite material to form a dental restoration. The presence of the fibrous filler in the resin provides improved resiliency and toughness and thus optimum handling properties and thus, impact strength of the resin. In one embodiment the randomly dispersed short fiber filled veneer is used to form a pontic or like structure on top or around the framework. Attention is directed to FIG. 1 which shows a structural component 10 and a pontic component 12 disposed on component 10. Structural component 10 is placed on supporting elements 13 of a testing apparatus. The soft composite herein which is used to form pontic 12 is flexible and easy to shape and mold.

A process for manufacturing a dental restoration comprises providing a structural component for use as the framework of a dental restoration such as a bridge. Composite resin filled with a fibrous filler of randomly dispersed fibers is disposed on the structural component in the form of a pontic or like form and cured thereon to form a dental restoration.

In another embodiment, both the soft PFC veneer and the brittle PFC veneer are used in the manufacture of a bridge to maximize bridge strength. Accordingly, a brittle PFC veneer (if present) is placed on that surface of the bridge which is subjected primarily or additionally to compressive forces. This will generally be on the occlusal surface of the bridge, which is subject to masticatory forces. Of course, veneers as presently manufactured may also be substituted in place of the brittle veneer.

Figure 4:
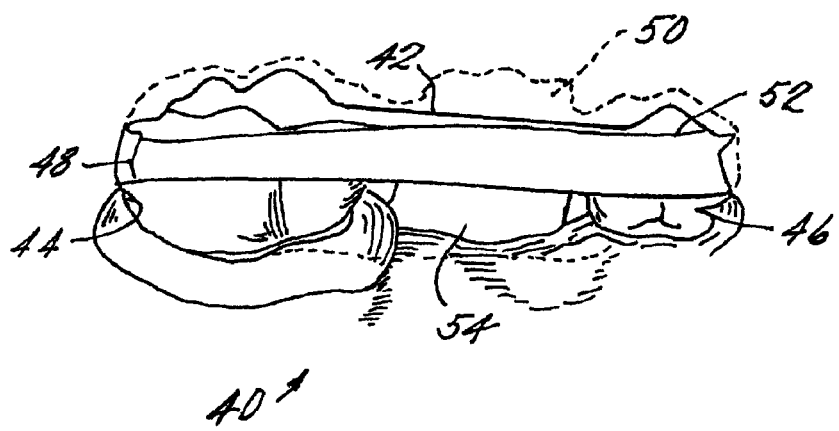
FIG. 4 is a perspective view of a dental bridge of the prior art located in the mandibular portion of the mouth.

For this reason, it is advantageous to place a soft PFC on the surface of the bridge which is expected to undergo primarily or additional tensile strain, i.e., on the gingival side, which is the side opposite to the surface subject to masticatory forces. The soft PFC may further be advantageously placed on the gingival half of the restoration. As shown in FIG. 4, a preferred bridge 40 in accordance with the present invention therefore comprises an FRC framework in the form of at least one bar 42 providing structural support for a bridge support between abutment teeth 44, 46. Preferably, the restoration comprises further FRC material 48 wrapped around abutments 44, 46. A brittle PFC veneer 50 is shown in shadow on the occlusal surface 52 of bridge 40, where it will be subject to compressive stresses arising from mastication. A soft PFC veneer 54 is shown in shadow on the gingival surface of bridge 40, where it will be subject to a tensile strain arising from mastication.

The stress/strain relationship of the materials is important to the embodiments described herein. It is important to note that in addition to the amount of fillers present in the veneers, filler dimensions, filler distribution, size distribution of the fillers, and the stress-strain behavior of the resin all effect the deflection properties of the resin. As shown in the formula below, strain is proportional to deflection which is inversely proportional to thickness of the sample.

$$r = 6Dd/L^2$$

wherein r=maximum strain at the bottom surface
D=maximum deflection at the center of the beam
L=support span; and
d=thickness of sample Since the deflection of the veneer is inversely proportional to the thickness, the deflection may increase as the thickness decreases.

The following non-limiting examples further describes the dental materials and restorations of the present invention.

EXAMPLE 1

Figure 2:
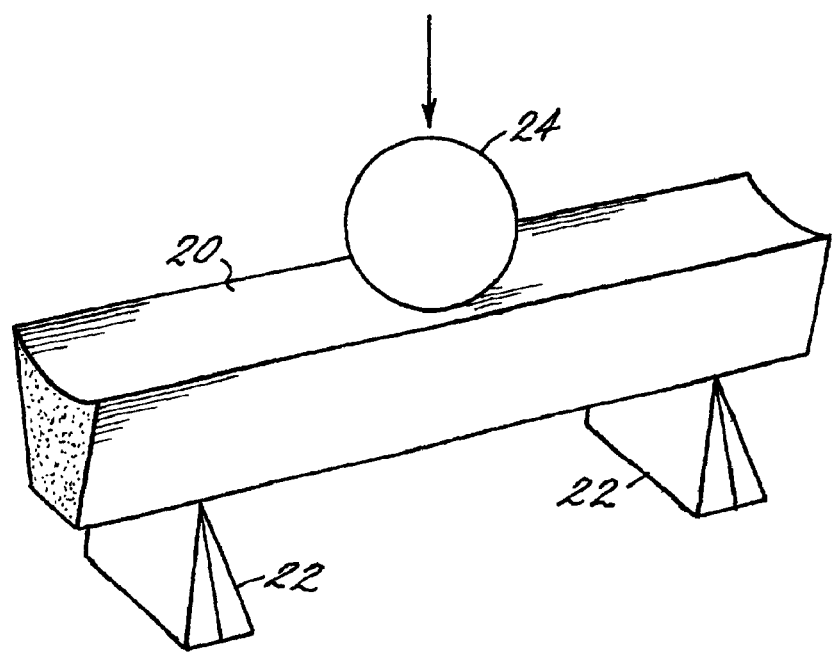
FIG. 2 is a perspective view of the testing arrangement utilized to measure three-point bend strength of various samples.

Three groups of bars were fabricated of different resin filled composite materials. Group A bars were composed of resin with standard particulate filler. Group B bars were composed of resin with short fibers randomly dispersed therein as disclosed herein. Group C bars were composed of resin having longitudinally extending fibers dispersed unidirectionally therein. Three-point bend testing was performed on the three groups of bars having dimensions of 4×3×25 mm. The average deflection of Group A bars was 0.44 mm. The average deflection of Group B bars was 0.683 mm. The average deflection of Group C bars was 0.647 mm. The testing shows that the deflection of the composite used in Group B is slightly greater than the deflection of the resin used in Group C. Thus, the resin of the invention comprising short random fibers is much more compatible than standard particulate filled resins to fiber reinforced resins used in the fabrication of structural components. The testing configuration is shown in FIG. 2 wherein a bar 20 is positioned on fulcrums 22 and a load in the shape of a ball 24 is applied at the midpoint of the bar to measure the bend strength thereof.

EXAMPLE 2

Figure 3:
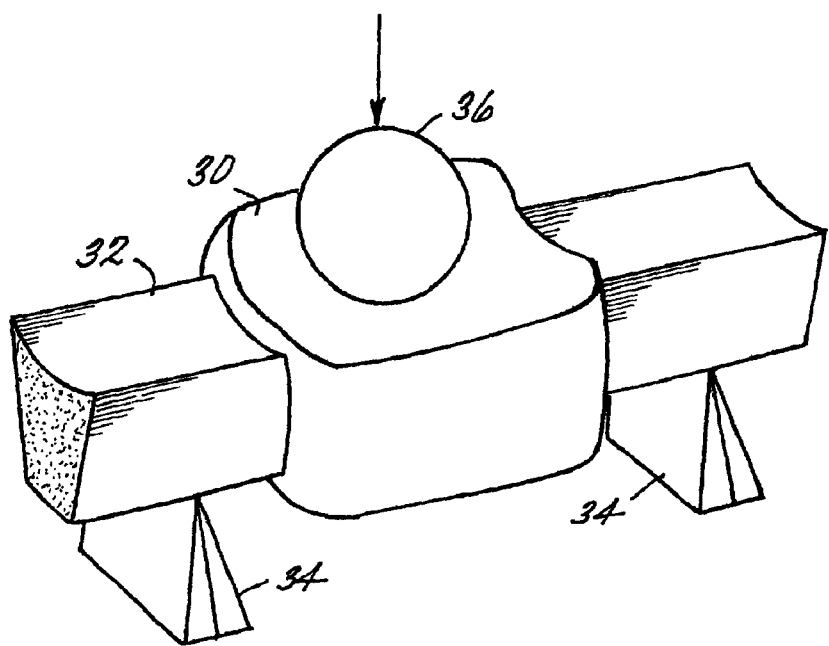
FIG. 3 is a perspective view of the testing arrangement utilized to measure three-point bend strength of various samples.

Fiber reinforced structural components in the shape of bars were provided and pontics were formed thereon using standard particulate filled resins (Group A) and using fiber filled resins of the invention (Group B). Three-point bend testing was conducted on Group A and Group B samples. Group B samples showed tremendously higher load bearing capability in comparison to Group A samples. Group A samples averaged an initial failure at about 141 pounds. Group B averaged an initial failure at about 257 pounds. The testing configuration is shown in FIG. 3 wherein a pontic 30 is disposed on a bar 32. Bar 32 rests on fulcrums 34. A load in the shape of a ball 36 is applied at the midpoint of the bar to measure the bend strength thereof.

EXAMPLE 3

The advantage of a bridge construction in accordance with the present invention is illustrated in three-point-bending flexural tests of bilayer samples of FRC and PFC veneers. Essentially rectangular bars of 4 mm×3 mm×25 mm were prepared with FRC and either a brittle particulate filled composite or a soft particulate filled composite. The FRC prepreg was prepared from S2-GLASS® fibers from Owens-Corning, Toledo, Ohio and a dimethacrylate based resin by a filament winding technique. Fiber content was about 38% by volume. Soft PFC prepreg was an unfilled ethoxylated BIS-GMA/PCDMA resin. Brittle PFC prepreg was 78% by weight inorganic barium borosilicate filler and 22% by weight ethoxylated BIS-GMA/PCDMA resin. Three-point-bending flexural tests were conducted according to ADA Specification No. 27. The results are shown in Table 3 below.

TABLE 3

| Sample | Size, mm* | Maximum Load (N) | Deflection (mm) |
|---|---|---|---|
| Top: FRC | 3 × 3 × 25 | 274 ± 52 | .23 ± .06 |
| Bottom: Brittle PFC | 1 × 3 × 25 | | |
| Top: FRC | 3 × 3 × 25 | 488 ± 17 | .50 ± .17 |
| Bottom: Soft FRC | 1 × 3 × 25 | | |

*thickness, width, length respectively

Average maximum flexural loads were 274±52 Newtons for FRC/brittle PFC bilayers, and 488±17 N for FRC/soft PFC bilayers, indicating more than a 75% increase in flexural load bearing capability when a soft PFC veneer is present on the gingival (tensional stress) surface.

EXAMPLE 4

Each PFC is characterized as either brittle or soft according to the deflection values listed in Table 4 below, which also lists maximum load for each sample. Rectangular bars of FRC and PFC material were fabricated for testing flexural strength and deflection using a three-point-bending flexural test. Single and double bars consisting of FRC and PFC materials were tested. The double bars consisted of a top layer of FRC material and a bottom layer of PFC material. Both soft and brittle PFC materials were used in combination with the FRC material by layering one on the other to form a simulation of a dental restoration having an FRC layer and one or more PFC layers. The results are shown in Table 4 below. The results demonstrate that the flexural strength of an FRC/brittle PFC bilayer is higher when force is applied normal to the brittle PFC (resulting in compressive stress on the brittle PFC), and lower when force is applied normal to the FRC side (resulting in the brittle PFC being under tensile stress). This result follows from the lower deflection of values of the brittle PFC samples compared to the deflection values of the FRC samples. It can therefore be concluded that when the brittle PFC layer is under tensile stress, the strength of an FRC/brittle PFC bilayer is limited by the low deflection of the brittle PFC.

TABLE 4

| Sample | Size, mm* | Maximum Load (N) | Average Deflection (mm) |
|---|---|---|---|
| Brittle PFC | 2 × 2 × 25 | 36.1 ± 4.1 | 0.5 |
| Soft PFC | 2 × 2 × 25 | 21.6 ± 2.7 | 4.5 |
| FRC | 1 × 2 × 25 | 81 ± 7.7 | 1.1 |
| Top: FRC<br>Bottom: Brittle PFC | 1 × 2 × 25<br>1 × 2 × 25 | 38.3 ± 5.5 | 0.5 |
| Top: FRC<br>Bottom: Soft FRC | 1 × 2 × 25<br>1 × 2 × 25 | 76.8 ± 4.8 | 2.6 |

*thickness, width, length respectively

Figure 5:
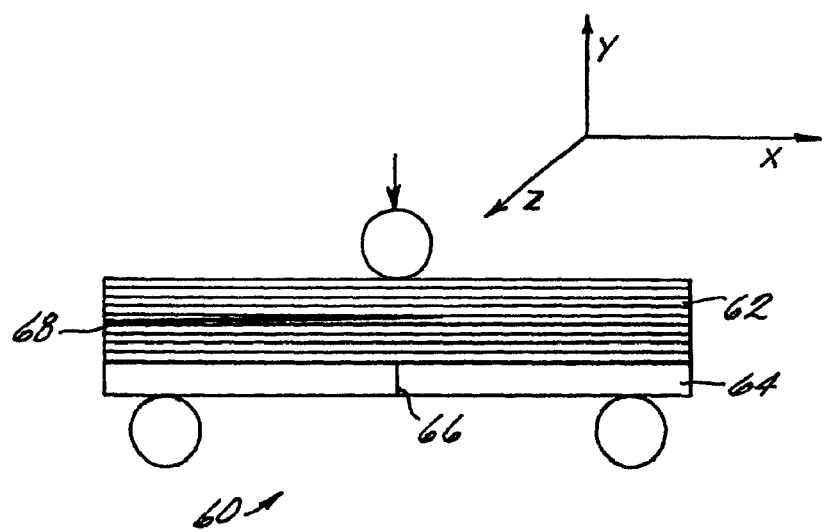
FIG. 5 is a perspective view of a fracture pattern in a prosthodontics material having a fiber reinforced framework component and a brittle particulate filled composite component.

FIG. 5 illustrates a sample 60 having an FRC 62 on the occlusal surface and a brittle PFC 64 on the gingival surface (and therefore subject to tensile stress) undergoing a three-point-bending flexural test. The first break 66 occurred perpendicular to the X-Z plane of brittle PFC 64, and was followed by the delamination 68 of FRC 62 along the X-Z plane.

Figure 6:
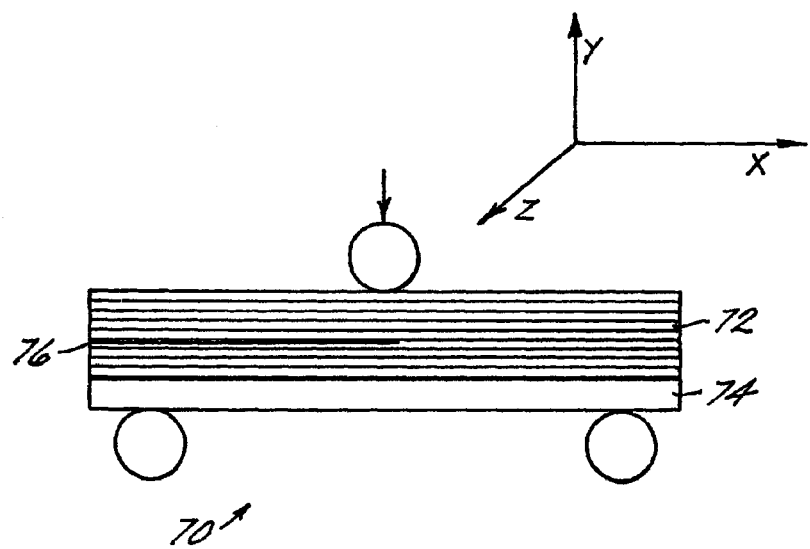
FIG. 6 is a perspective view of a fracture pattern in a prosthodontics material having a fiber reinforced framework component and a soft particulate filled composite component.

FIG. 6 illustrates sample 70 having FRC 72 on the occlusal surface and a soft PFC 74 on the gingival surface (and therefore subject to tensile stress) undergoing a three-point-bending flexural test. In contrast to the above results, the first break for this sample arose from delamination 76 of FRC 72 along the X-Z plane.

Table 4 shows the data for different configurations of test specimens and materials. The average flexural loads were 38.3±5.5 Newtons for the FRC/brittle PFC bilayers and 76.8±4.8 for the FRC/soft PFC bilayers. The latter is approaching the average maximum flexural load of 81±7.7 N for FRC material alone. Use of a soft PFC veneer on gingival surface of a dental bridge will therefore lead to increased performance of the bridge.

As will be appreciated, the present invention provides a superior resin composite which is compatible with fiber reinforced composite structural components and which provides high strength dental restorations.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed:

1. A dental restoration comprising:
a fiber-reinforced structural component having fibers greater than 10 mm in length embedded within a first polymeric matrix material; and
a pontic disposed on the structural component, the pontic having randomly dispersed fibers with maximum lengths no greater than ¼ inch embedded within a second polymeric matrix material wherein the first and second polymeric matrix are the same or different.

2. The dental restoration of claim 1 wherein the pontic comprises fibers having lengths in the range from about 0.01 to about 6 mm.

3. The dental restoration of claim 1 wherein the fibers embedded within the first polymeric matrix are oriented, woven, longitudinally distributed, normally oriented to a longitudinal axis, or a mixture thereof.

4. The dental restoration of claim 1 wherein the strain to failure value of the pontic is about equal to or higher than the strain to failure value of the structural component.

5. The dental restoration of claim 1 wherein the randomly dispersed fibers are selected from the group consisting of glass, carbon, ceramic, graphite, polyaramid fibers, and combinations of two or more of the foregoing.

6. The dental restoration of claim 1 wherein the pontic further comprises a particulate filler.

7. The dental restoration of claim 6 wherein the particulate filler is selected from the group consisting of a silica, silicate glass, quartz, barium borosilicate, strontium silicate, barium silicate, strontium borosilicate, borosilicate, lithium silicate, amorphous silica, calcium phosphate, alumina, zirconia, tin oxide, titania, and combinations of two or more of the foregoing.

8. A process for forming a dental restoration comprising:
providing a structural element comprised of a first fiber reinforced composite material;
disposing a second composite material thereon, wherein the second composite material comprises randomly dispersed fibers embedded within a polymeric material; and
curing the second composite material.

9. The process of claim 8 wherein the structural component is cured prior to disposing the second composite material thereon.

10. A dental restoration comprising:
a fiber-reinforced structural component having fibers embedded within a first polymeric matrix material; and
a pontic disposed on the structural component, the pontic having randomly dispersed fibers embedded within a second polymeric matrix material wherein the first and second polymeric matrix are the same or different and the fibers embedded within the first polymeric matrix are not randomly dispersed relative to each other.

11. The dental restoration of claim 10 wherein the randomly dispersed fibers have maximum lengths no greater than ¼ inch.

12. The dental restoration of claim 10 wherein the pontic comprises fibers having lengths from about 0.01 to about 6 mm.

13. The dental restoration of claim 10 wherein the fibers embedded within the first polymeric matrix are oriented, woven, longitudinally distributed, normally oriented to a longitudinal axis, or a mixture thereof.

14. The dental restoration of claim 10 wherein the strain to failure value of the pontic is about equal to or higher than the strain to failure value of the structural component.

15. The dental restoration of claim 10 wherein the randomly dispersed fibers are selected from the group consisting of glass, carbon, ceramic, graphite, polyaramid fibers, and combinations of two or more of the foregoing.

16. The dental restoration of claim 10 wherein the pontic further comprises a particulate filler.

17. The dental restoration of claim 16 wherein the particulate filler is selected from the group consisting of a silica, silicate glass, quartz, barium borosilicate, strontium silicate, barium silicate, strontium borosilicate, borosilicate, lithium silicate, amorphous silica, calcium phosphate, alumina, zirconia, tin oxide, titania, and combinations of two or more of the foregoing.

* * * * *